US009788910B2

(12) United States Patent
Schuh

(10) Patent No.: US 9,788,910 B2
(45) Date of Patent: Oct. 17, 2017

(54) INSTRUMENT-MOUNTED TENSION SENSING MECHANISM FOR ROBOTICALLY-DRIVEN MEDICAL INSTRUMENTS

(71) Applicant: Auris Surgical Robotics, Inc., San Carlos, CA (US)

(72) Inventor: Travis Schuh, Los Altos, CA (US)

(73) Assignee: Auris Surgical Robotics, Inc., San Carlos, CA (US)

( * ) Notice: Subject to any disclaimer, the term of this patent is extended or adjusted under 35 U.S.C. 154(b) by 0 days.

(21) Appl. No.: 15/188,802

(22) Filed: Jun. 21, 2016

(65) Prior Publication Data

US 2016/0374766 A1 Dec. 29, 2016

Related U.S. Application Data

(60) Provisional application No. 62/184,741, filed on Jun. 25, 2015.

(51) Int. Cl.
*A61B 34/30* (2016.01)
*A61M 25/01* (2006.01)
(Continued)

(52) U.S. Cl.
CPC ............ *A61B 34/30* (2016.02); *A61B 5/4523* (2013.01); *A61B 5/6852* (2013.01);
(Continued)

(58) Field of Classification Search
CPC ............ G01L 5/101–5/108; G01L 5/10; A61B 2034/301; A61B 1/0057; A61B 34/71; A61M 25/0147
(Continued)

(56) References Cited

U.S. PATENT DOCUMENTS 4,141,245 A * 2/1979 Brandstetter ........... G01L 3/247
474/109
4,241,884 A * 12/1980 Lynch .................... B65H 49/34
241/73
(Continued)

FOREIGN PATENT DOCUMENTS

DE 102004020465 B3 * 9/2005 ............. B65H 59/16
EP 2392435 A2 12/2011
(Continued)

OTHER PUBLICATIONS

Balicki, et al. Single fiber optical coherence tomography microsurgical instruments for computer and robot-assisted retinal surgery. Medical Image Computing and Computer-Assisted Intervention. MICCAI 2009. Springer Berlin Heidelberg, 2009. 108-115.
(Continued)

*Primary Examiner* — Kevin C Sirmons
*Assistant Examiner* — William Carpenter
(74) *Attorney, Agent, or Firm* — Knobbe Martens Olson & Bear LLP

(57) ABSTRACT

A tension mechanism for a robotically-controlled medical device measures the tension applied to an actuation tendon to provide feedback to a robotic controller. In one embodiment, the device comprises an elongated instrument, an elongated member, and a base. The elongated member is coupled to the distal end of the elongated instrument, configured to actuate the distal end of the elongated instrument in response to tension in the elongated member. The base is located at the proximal end of the elongated instrument, and comprises a first redirect surface that redirects the elongated member. The first redirect surface is coupled to a lever element that is configured to exert a reactive force on a sensor in response to tension in the elongated member.

29 Claims, 15 Drawing Sheets

(51) Int. Cl.
*A61B 5/00* (2006.01)
*G01L 5/04* (2006.01)

(52) U.S. Cl.
CPC ... *A61M 25/0147* (2013.01); *A61B 2034/301* (2016.02); *A61B 2562/0252* (2013.01); *A61B 2562/0261* (2013.01); *G01L 5/04* (2013.01)

(58) Field of Classification Search
USPC ............. 73/862.292, 862.393; 242/416, 418, 242/418.1, 419.1, 420, 420.5, 420.6
See application file for complete search history.

(56) References Cited

U.S. PATENT DOCUMENTS

| | | | |
|---|---|---|---|
| 4,351,493 A * | 9/1982 | Sonnek | G11B 15/43 242/420.6 |
| 4,530,471 A * | 7/1985 | Inoue | B23H 7/10 219/69.12 |
| 4,597,388 A | 7/1986 | Koziol et al. | |
| 4,905,673 A | 3/1990 | Pimiskern | |
| 5,425,735 A | 6/1995 | Rosen et al. | |
| 5,472,406 A | 12/1995 | De La Torre et al. | |
| 5,572,999 A | 11/1996 | Funda et al. | |
| 5,662,590 A | 9/1997 | De La Torre et al. | |
| 5,695,500 A | 12/1997 | Taylor et al. | |
| 6,033,371 A | 3/2000 | Torre et al. | |
| 6,326,616 B1 | 12/2001 | Andrien et al. | |
| 6,398,792 B1 | 6/2002 | O'Connor | |
| 6,406,486 B1 | 6/2002 | De La Torre et al. | |
| 6,436,107 B1 | 8/2002 | Wang et al. | |
| 6,554,793 B1 | 4/2003 | Pauker et al. | |
| 6,638,246 B1 | 10/2003 | Naimark et al. | |
| 6,671,581 B2 | 12/2003 | Niemeyer et al. | |
| 6,736,784 B1 | 5/2004 | Menne et al. | |
| 6,763,259 B1 | 7/2004 | Hauger et al. | |
| 7,087,061 B2 | 8/2006 | Chernenko et al. | |
| 7,344,528 B1 | 3/2008 | Tu et al. | |
| 7,351,193 B2 | 4/2008 | Forman et al. | |
| 7,725,214 B2 | 5/2010 | Diolaiti | |
| 7,883,475 B2 | 2/2011 | Dupont et al. | |
| 7,967,799 B2 | 6/2011 | Boukhny | |
| 8,049,873 B2 | 11/2011 | Hauger et al. | |
| 8,224,484 B2 | 7/2012 | Swarup et al. | |
| 8,414,564 B2 | 4/2013 | Goldshleger et al. | |
| 8,518,024 B2 | 8/2013 | Williams et al. | |
| 9,226,796 B2 | 1/2016 | Bowling et al. | |
| 2004/0030349 A1 | 2/2004 | Boukhny | |
| 2004/0257021 A1 | 12/2004 | Chang et al. | |
| 2005/0070844 A1 | 3/2005 | Chow et al. | |
| 2005/0222714 A1 | 10/2005 | Nihei et al. | |
| 2007/0032906 A1 | 2/2007 | Sutherland et al. | |
| 2007/0135733 A1 | 6/2007 | Soukup et al. | |
| 2007/0135763 A1 | 6/2007 | Musbach et al. | |
| 2007/0299427 A1 | 12/2007 | Yeung et al. | |
| 2008/0065109 A1 | 3/2008 | Larkin | |
| 2008/0097293 A1 | 4/2008 | Chin et al. | |
| 2008/0114341 A1 | 5/2008 | Thyzel | |
| 2008/0177285 A1 | 7/2008 | Brock et al. | |
| 2008/0187101 A1 | 8/2008 | Gertner | |
| 2008/0228104 A1 | 9/2008 | Uber et al. | |
| 2008/0231221 A1 | 9/2008 | Ogawa | |
| 2008/0262301 A1 * | 10/2008 | Gibbons | A61B 1/00082 600/114 |
| 2009/0171271 A1 | 7/2009 | Webster et al. | |
| 2009/0248041 A1 | 10/2009 | Williams et al. | |
| 2009/0248043 A1 | 10/2009 | Tierney et al. | |
| 2009/0264878 A1 | 10/2009 | Carmel et al. | |
| 2009/0268015 A1 | 10/2009 | Scott et al. | |
| 2009/0287354 A1 | 11/2009 | Choi | |
| 2009/0312768 A1 | 12/2009 | Hawkins et al. | |
| 2009/0326322 A1 | 12/2009 | Diolaiti | |
| 2010/0036294 A1 | 2/2010 | Mantell et al. | |
| 2010/0073150 A1 | 3/2010 | Olson et al. | |
| 2010/0256812 A1 | 10/2010 | Tsusaka et al. | |
| 2011/0009779 A1 | 1/2011 | Romano et al. | |
| 2011/0015648 A1 * | 1/2011 | Alvarez | A61B 34/71 606/130 |
| 2011/0028887 A1 | 2/2011 | Fischer et al. | |
| 2011/0040404 A1 | 2/2011 | Diolaiti et al. | |
| 2011/0046441 A1 | 2/2011 | Wiltshire et al. | |
| 2011/0106102 A1 | 5/2011 | Balicki et al. | |
| 2011/0306836 A1 | 12/2011 | Ohline et al. | |
| 2012/0138586 A1 | 6/2012 | Webster et al. | |
| 2012/0283747 A1 | 11/2012 | Popovic | |
| 2013/0144116 A1 | 6/2013 | Cooper et al. | |
| 2013/0317519 A1 * | 11/2013 | Romo | A61B 34/30 606/130 |
| 2013/0325030 A1 | 12/2013 | Hourtash et al. | |
| 2014/0012276 A1 | 1/2014 | Alvarez | |
| 2014/0135985 A1 | 5/2014 | Coste-Maniere et al. | |
| 2014/0276594 A1 | 9/2014 | Tanner et al. | |
| 2014/0296870 A1 | 10/2014 | Stern et al. | |
| 2014/0309649 A1 | 10/2014 | Alvarez et al. | |
| 2014/0364870 A1 | 12/2014 | Alvarez et al. | |
| 2014/0379000 A1 | 12/2014 | Romo et al. | |
| 2015/0025539 A1 | 1/2015 | Alvarez et al. | |
| 2015/0051592 A1 | 2/2015 | Kintz | |
| 2015/0101442 A1 | 4/2015 | Romo | |
| 2015/0104284 A1 | 4/2015 | Riedel | |
| 2015/0119637 A1 | 4/2015 | Alvarez et al. | |
| 2015/0119638 A1 | 4/2015 | Yu et al. | |
| 2015/0148600 A1 * | 5/2015 | Ashinuma | A61B 1/0057 600/109 |
| 2015/0164594 A1 | 6/2015 | Romo et al. | |
| 2015/0164595 A1 | 6/2015 | Bogusky et al. | |
| 2015/0164596 A1 | 6/2015 | Romo et al. | |
| 2015/0342695 A1 | 12/2015 | He et al. | |

FOREIGN PATENT DOCUMENTS

| | | | | |
|---|---|---|---|---|
| JP | H09224951 A | | 9/1997 | |
| JP | WO 2013179600 A1 * | | 12/2013 | ........... A61B 1/0057 |
| WO | WO 92/14411 A1 | | 9/1992 | |
| WO | WO 03/096871 A2 | | 11/2003 | |
| WO | WO 2004/105849 A1 | | 12/2004 | |
| WO | WO 2011/161218 A1 | | 12/2011 | |

OTHER PUBLICATIONS

Effect of microsecond pulse length and tip shape on explosive. bubble formation of2.78 iLtm Er,Cr;YSGG and 2.94 iLtm Er:YAG laser. Paper 8221-12, Proceedings of SPIE, vol. 8221 (Monday Jan. 23, 2013).
Ehlers, et al. Integration of a spectral domain optical coherence tomography system into a surgical microscope for intraoperative imaging. Investigative Ophthalmology and Visual Science 52.6. 2011; 3153-3159.
European search report and search opinion dated Jul. 2, 2015 for EP Application No. 12856685.8.
Hubschman. Robotic Eye Surgery: Past, Present, and Future. Journal of Computer Science and Systems Biology. 2012.
International search report and written opinion dated Mar. 29, 2013 for PCT/US2012/069540.
International search report and written opinion dated Nov. 7, 2014 for PCT Application No. US2014/041990.
International search report dated Jun. 16, 2014 for PCT/US2014/022424.
International search report and written opinion dated Jan. 27, 2015 for PCT Application No. US2014/062284.
Office action dated Jun. 19, 2014 for U.S. Appl. No. 13/868,769.
Office action dated May 21, 2015 for U.S. Appl. No. 13/711,440.
Office action dated Jun. 11, 2015 for U.S. Appl. No. 14/158,548.
Office action dated Oct. 7, 2014 for U.S. Appl. No. 13/711,440.
PCT International Search Report and Written Opinion, PCT Application No. PCT/US15/53306, Feb. 4, 2016, 19 pages.
Stoyanov. Surgical vision. Annals ofBiomedical Engineering40.2. 2012; 332-345. Published I 0/20/2011.
U.S. Appl. No. 62/019,816, filed Jul. 1, 2014, Inventors Enrique Romo et al.

(56) References Cited

OTHER PUBLICATIONS

U.S. Appl. No. 62/037,520, filed Aug. 14, 2014, Inventor Alan Yu.
U.S. Appl. No. 62/057,936, filed Sep. 30, 2014, Inventors Enrique Romo et al.
U.S. Appl. No. 62/140,344, filed Mar. 30, 2015.
U.S. Appl. No. 14/578,082, filed Dec. 19, 2014, Inventors Alvarez et al.
U.S. Appl. No. 14/583,021, filed Dec. 24, 2014, Inventors Romo et al.
U.S. Appl. No. 14/542,373, filed Nov. 14, 2014, Inventors Romo et al.
U.S. Appl. No. 14/542,387, filed Nov. 14, 2014, Inventors Bogusky et al.
U.S. Appl. No. 14/542,403, filed Nov. 14, 2014, Inventors Yu et al.
U.S. Appl. No. 14/542,429, filed Nov. 14, 2014, Inventors Romo et al.
U.S. Appl. No. 14/196,953, filed Mar. 4, 2014, Inventors Jeffery B. Alvarez et al.
U.S. Appl. No. 14/201,610, filed Mar. 7, 2014, Inventor Enrique Romo.
U.S. Appl. No. 14/301,871, filed Jun. 11, 2014, Inventors Jeffery B. Alvarez et al.
U.S. Appl. No. 14/301,871, filed Aug. 12, 2014, Inventors Jeffery B. Alvarez et al.
U.S. Appl. No. 14/479,095, filed Sep. 5, 2014, Inventors Enrique Romo et al.

\* cited by examiner

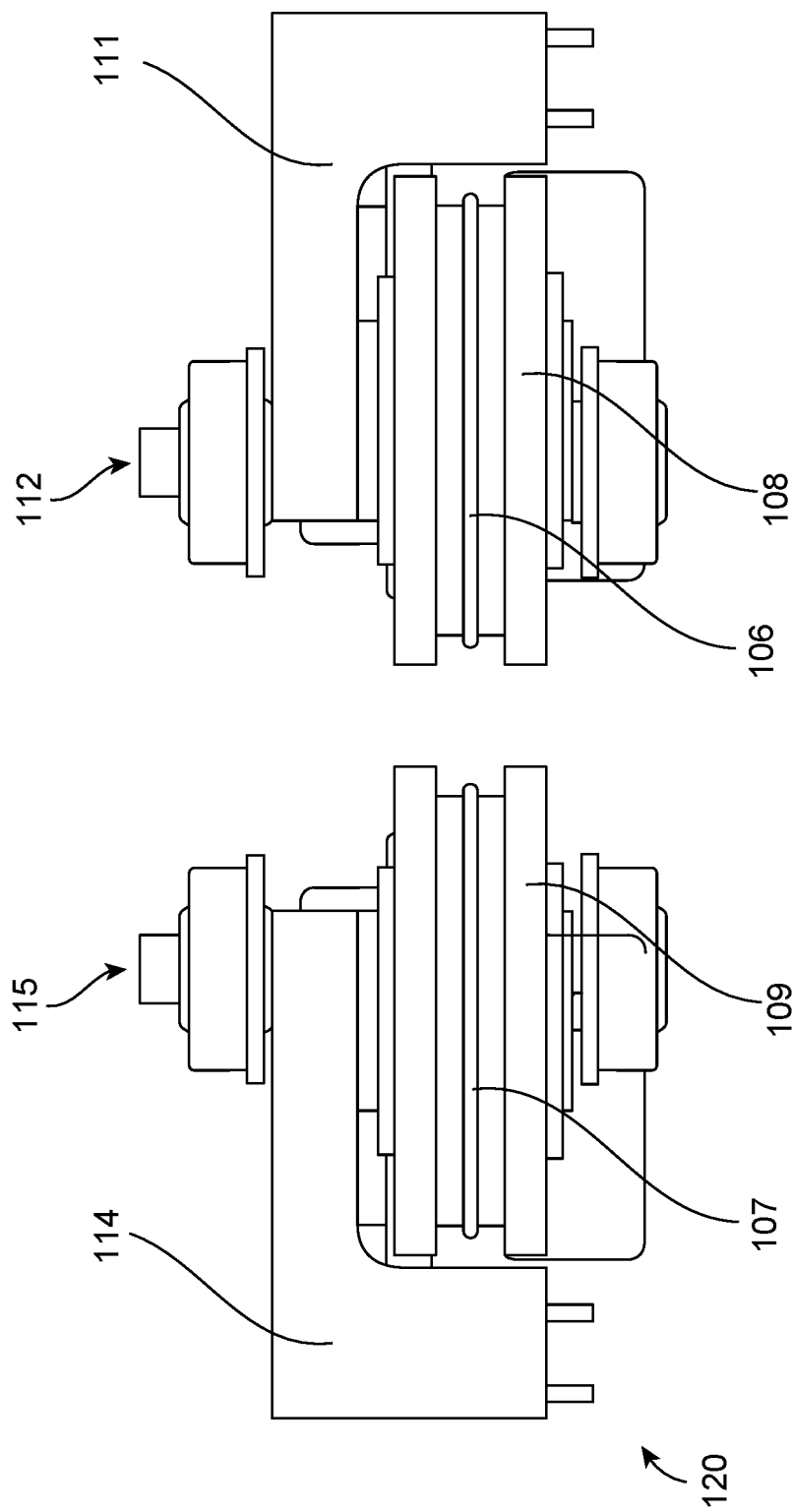

INSTRUMENT-MOUNTED TENSION SENSING MECHANISM FOR ROBOTICALLY-DRIVEN MEDICAL INSTRUMENTS

CROSS-REFERENCE TO RELATED APPLICATIONS

This application claims the benefit of and priority to U.S. Provisional Application No. 62/184,741 filed Jun. 25, 2015, the entire contents of which are incorporated herein by reference. This application is related to U.S. patent application Ser. No. 14/523,760, filed Oct. 24, 2014, U.S. Provisional Patent Application No. 62/019,816, filed Jul. 1, 2014, U.S. Provisional Patent Application No. 62/037,520, filed Aug. 14, 2014, U.S. Provisional Patent Application No. 62/057,936, filed Sep. 30, 2014, and U.S. Provisional Patent Application No. 62/140,344, filed Mar. 30, 2015, the entire contents of which are incorporated herein by reference.

BACKGROUND

1. Field of Art

This description generally relates to surgical robotics, and particularly to an instrument-mounted tension sensing design that may be used in conjunction with a medical robotics platform for a number of surgical procedures. More particularly, the field of the invention pertains to instrument-mounted tension sensing mechanisms that detect tension in actuation tendons, such as those used to operate robotically-controlled tools to perform diagnostic and therapeutic surgical procedures.

2. Description of the Related Art

Use of robotic technologies presents a number of advantages over traditional, manual surgery procedures. In particular, robotic surgeries often allow for greater precision, control, and access. Robotically-controlled technologies, however, sometimes create engineering challenges that require creative engineering workarounds. In the case of robotically-controlled tools, the use of actuation tendons to operate robotic laparoscopic tools and catheters gives rise to control problems that often requires very precise monitoring of the actuation tendons. Over the lifespan of an actuation tendon, the tendon may stretch and deform, and over time exhibit greater non-linearity with respect to instrument tip displacement relative to the tension applied to the tendon. Accordingly, within a robotically-controlled instrument, there is a need to measure the tension applied to the actuation tendon to provide feedback to the control robotic controller. Accordingly, there is a need for an instrument-mounted tension sensing mechanism.

SUMMARY

In general, the present invention provides for a medical device comprising an elongated instrument, an elongated member coupled to the distal end of the elongated instrument, configured to actuate the distal end of the elongated instrument in response to tension in the elongated member, and a base located at the proximal end of the elongated instrument, the base comprising redirect surface that redirects the elongated member, wherein the first redirect surface is coupled to a lever element that is configured to exert a reactive force on a sensor in response to tension in the elongated member.

In one aspect, the first redirect surface is low friction. In one aspect, the first redirect surface comprises a first rotatable body. In one aspect, the base further comprises a second rotatable body, wherein the elongated member is threaded around the second rotatable body. In one aspect, rotational motion of the second rotatable body is configured to cause tension in the elongated member. In one aspect, the second rotatable body comprises splines that receive rotational motion through a sterile interface from the robotic drive mechanism. In one aspect, the second rotatable body is a male connector. In one aspect, the second rotatable body is a female connector.

In another aspect, the lever element is constrained by a pivot point on a first location of the lever element and the sensor on a second location of the lever element. In one aspect, the pivot point of the lever element is offset from the axis of the first rotatable body.

In another aspect, the ratio of the tension in the elongated member to the reactive force on the sensor is fixed. In one aspect, the lever element is configured to distribute the tension in the elongated member between the pivot point and the sensor. In one aspect, the elongated instrument is flexible. In one aspect, the elongated instrument is a catheter. In one aspect, the elongated instrument is rigid. In one aspect, the base is configured to interface with a robotic drive mechanism. In one aspect, the elongated member is at least one of a wire, cable, and a tendon. In one aspect, the sensor is at least one of a load cell, a piezoresistive device, a piezoelectric device, and a strain gauge.

BRIEF DESCRIPTION OF DRAWINGS

FIGS. 1C, 1D, 1E, 1F, 1G illustrate additional views of the robotically-controlled instrument from FIGS. 1A, 1B, in accordance with an embodiment of the present invention.

Reference will now be made in detail to several embodiments, examples of which are illustrated in the accompanying figures. It is noted that wherever practicable similar or like reference numbers may be used in the figures and may indicate similar or like functionality. The figures depict embodiments of the described system (or method) for purposes of illustration only. One skilled in the art will readily recognize from the following description that alternative embodiments of the structures and methods illustrated herein may be employed without departing from the principles described herein.

DETAILED DESCRIPTION

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

To guarantee control fidelity, it may be important to monitor the tendon tension when robotically-controlling endoscopic and laparoscopic tools that use tendon-like members, such as a catheter, endoscope, laparoscopic grasper, or forceps. While there are a number of approaches to monitoring tendon tension, direct measurement in the instrument provides a number of practical advantages, including simplifying the instrument-driver interface, and reduce friction and inefficiencies in transmission through the interface. Accordingly, the present invention provides a sensing apparatus that may be mounted within the instrument.

Figure 1A:
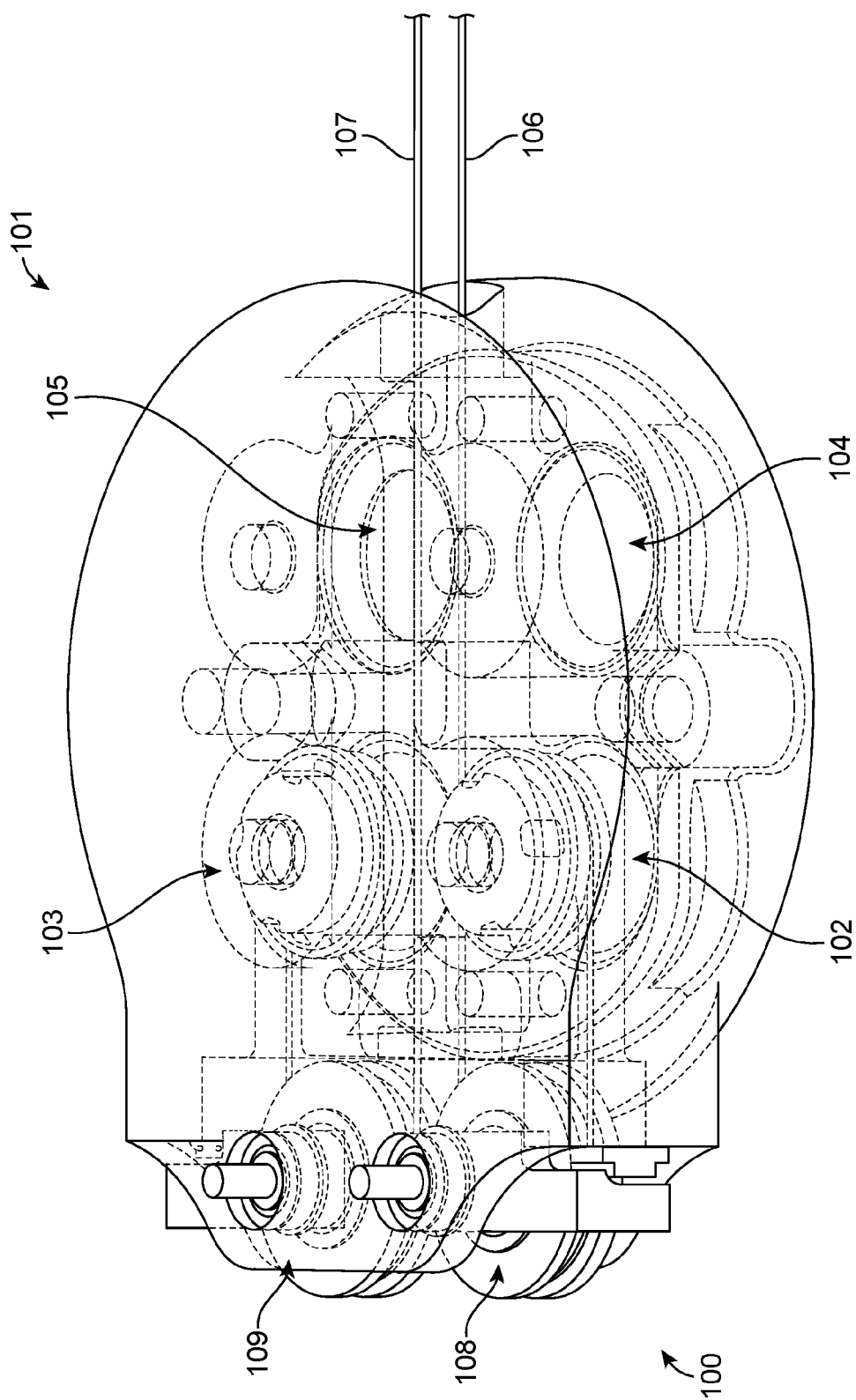
FIG. 1A illustrates a tension sensing mechanism located within a robotically-controlled instrument, in accordance with an embodiment of the present invention.

FIG. 1A illustrates a tension sensing mechanism located within the robotically-controlled instrument, in accordance with an embodiment of the present invention. In transparent isometric view 100, the instrument 101 provides for a series of actuating bodies, such as rotatable bodies for low friction, such as spools or pulleys 102, 103, that are coupled to tendons 106 and 107 that are designed to actuate the distal end of an elongated instrument (not shown), such as a flexible catheter or rigid laparoscopic tool, in response to tension. Instrument 101 also provides for cavities 104, 105 for additional rotatable bodies to actuate additional tendons (now shown). Rotatable bodies 102, 103, and those potentially used in cavities 104, 105 may be driven by a robotically-controlled instrument device manipulator as part of a larger robotic system, such as those disclosed in the aforementioned patents. While the instrument 101 is shown to be circular, other embodiments may take other shapes, such as oblong, rectangular, or square-shaped.

In addition to the actuating rotatable bodies, and related cavities for additional rotatable bodies, the present embodiment contemplates redirecting surfaces, represented as rotatable (body) pulleys 108 and 109 in instrument 101, to measure tension in tendons 106 and 107 respectively. To measure tension, tendons 106 and 107 may be wound around rotatable bodies 108 and 109 in addition to rotatable bodies 102 and 103.

Figure 1B:
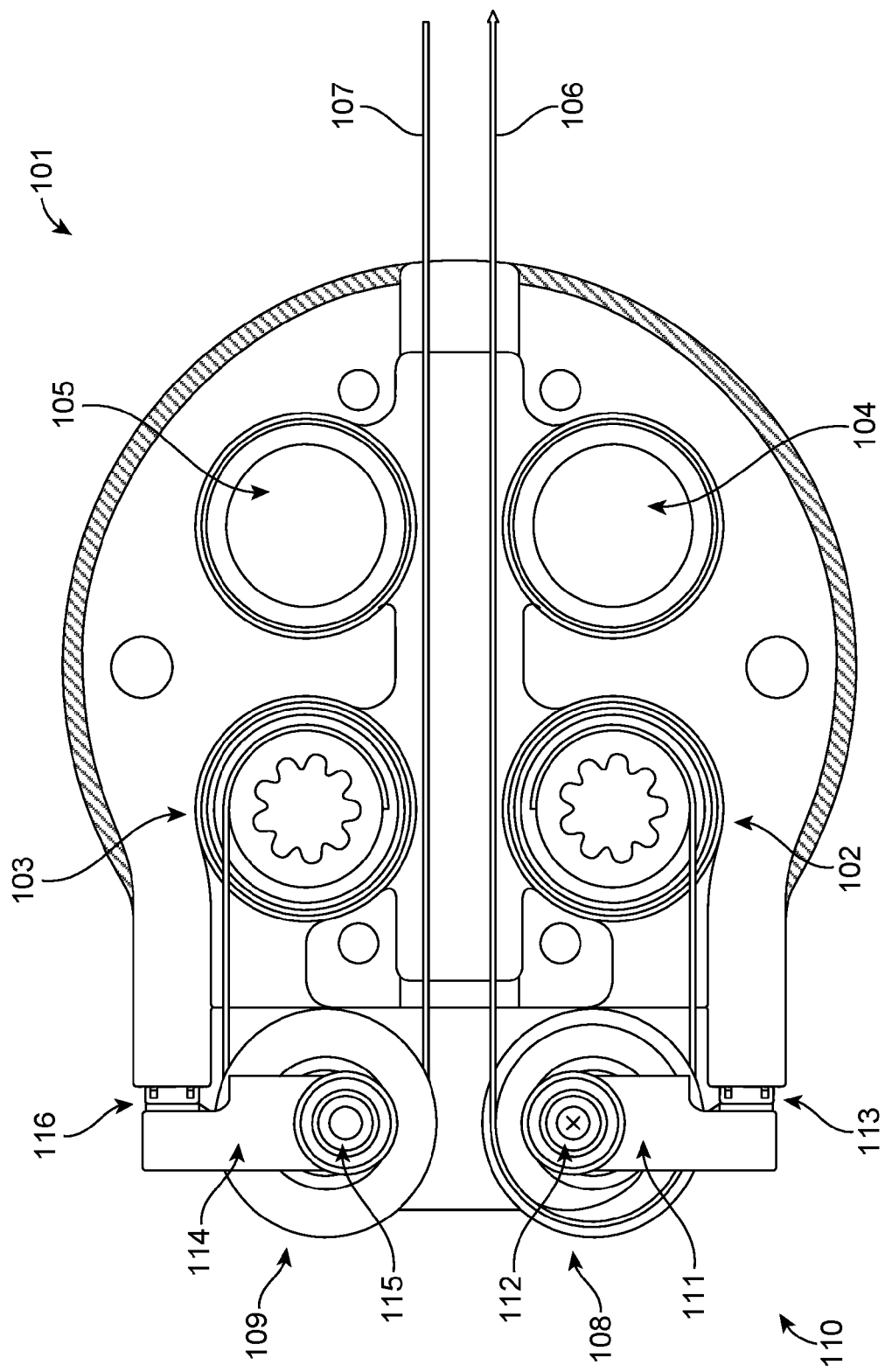
FIG. 1B illustrates a top schematic view of the robotically-controlled instrument of FIG. 1A, in accordance with an embodiment of the present invention.

FIG. 1B illustrates a top schematic view of the instrument 101, in accordance with an embodiment of the present invention. As shown in view 110, tendon 106 may be wound around pulley 102 and pulley 108. Similarly, tendon 107 may be wound around pulley 103 and pulley 109. Even though pulleys 102, 103, 108, 109 are shown to have parallel axes in instrument 101, they may not be parallel in other embodiments.

Pulley 108 is coupled to a lever element 111, which is configured to exert a reactive force in response to tension in tendon 106. The resulting reactive force from tension in tendon 106 may be resolved through contact between lever 111, constrained by a pivot point such as pivot axis 112, and sensor 113. While the instrument 101 contemplates the pivot axis 112 and sensor 113 positioned at opposite ends of the level element 111, they may be positioned at a number of positions along the lever element in other embodiments. The relative position of the sensor and pivot point may provide for a known, fixed ratio between the tension and the reactive force on the sensor. Identical structural relationships exist with respect to pulley 109, lever element 114, pivot axis 115, and sensor 116.

In some embodiments, the sensors 113 and 116 may be force sensors, piezoelectric sensors, piezoresistive sensors, or load cells to measure the reactive force exerted by levers 111 and 114 respectively. In some embodiments, it may be desirable for the sensors to be low cost, particularly if the instrument is intended to be recyclable or disposable.

In some embodiments, such as instrument 101, the pivot point may be offset from the axis of the corresponding rotatable body, e.g., the axis of pulley 108 relative to the pivot axis 112 in instrument 101. As shown in instrument 101, while the pivot point may be a pivot axis 112, which reduces friction resulting from any bending moments, the pivot point may be non-axial element in other embodiments, such as a flexure.

Tension on tendon 106 may be the consequence of a number factors, including rotation of pulley 108 or external pressure on the elongated member in which tendon 106 resides. Regardless of its source, when wound around pulley 108, tension on tendon 106 may be imparted equally around pulley 108. As the pulley 108 is operatively coupled to lever 111, the resulting reactive force may be transmitted through the lever 111 and measured based on the force exerted on sensor 113. The positioning of the lever 111, in contact with sensor 113, allows measurement of the reactive force from the tension in tendon 106.

Offsetting the axis of the pivot point such as pivot axis 112 at fixed distance from the axis of pulley 108 allows the force from lever 111 to be smaller or larger in magnitude based on the length of the lever and the fixed offset. Using these measurements, combined with the measured force at the sensor 113, the tension in tendon 106 may be calculated. Allowing for differences in the magnitude of the lever force based on the length of the lever may be useful to bring the measured force within the range and tolerances of the sensor. This may be particularly useful for inexpensive sensors designed for a specific range of forces. Identical operational relationships exist with respect to pulley 109, lever element 114, pivot axis 115, and sensor 116.

Among other advantages, this method of direct measurement of the tendon tension bypasses the complexity and efficiency losses that may be associated with measuring force further down the drivetrain.

Figure 1C:
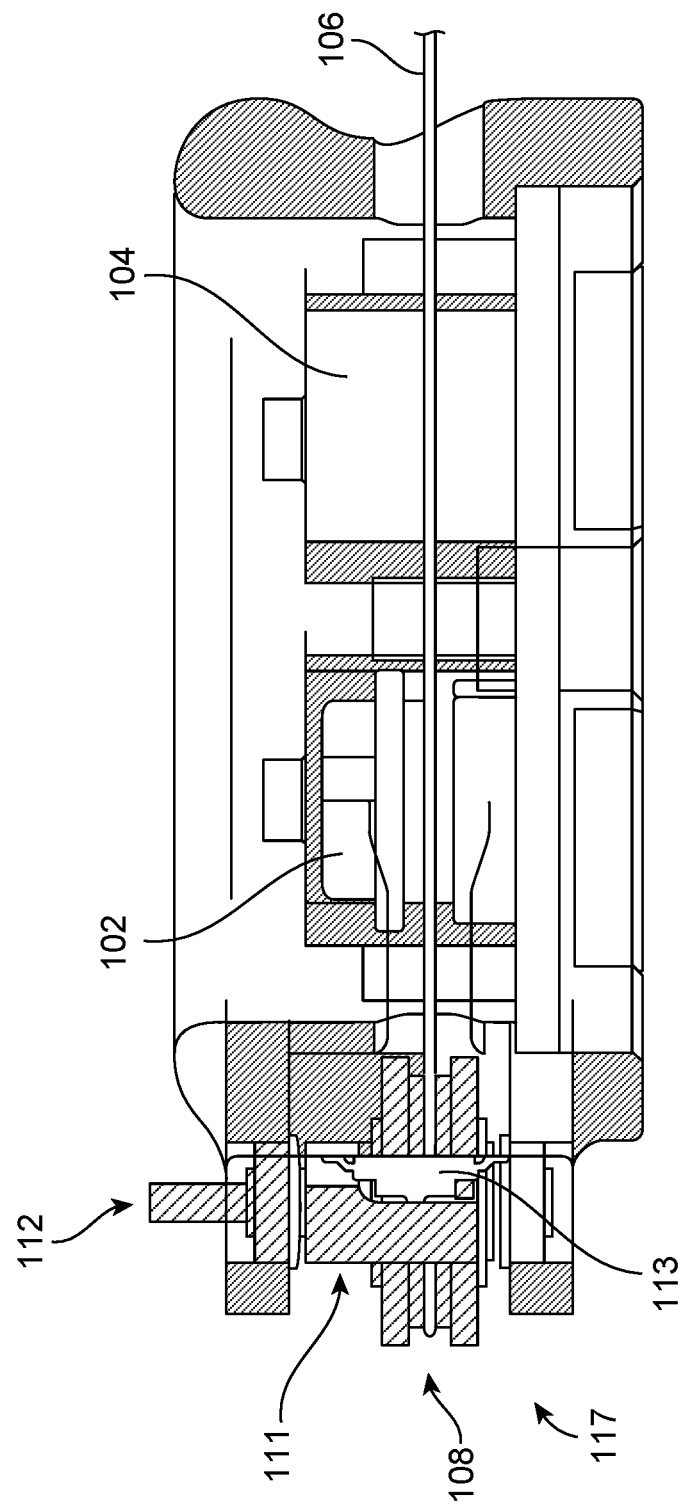
Figure 1D:
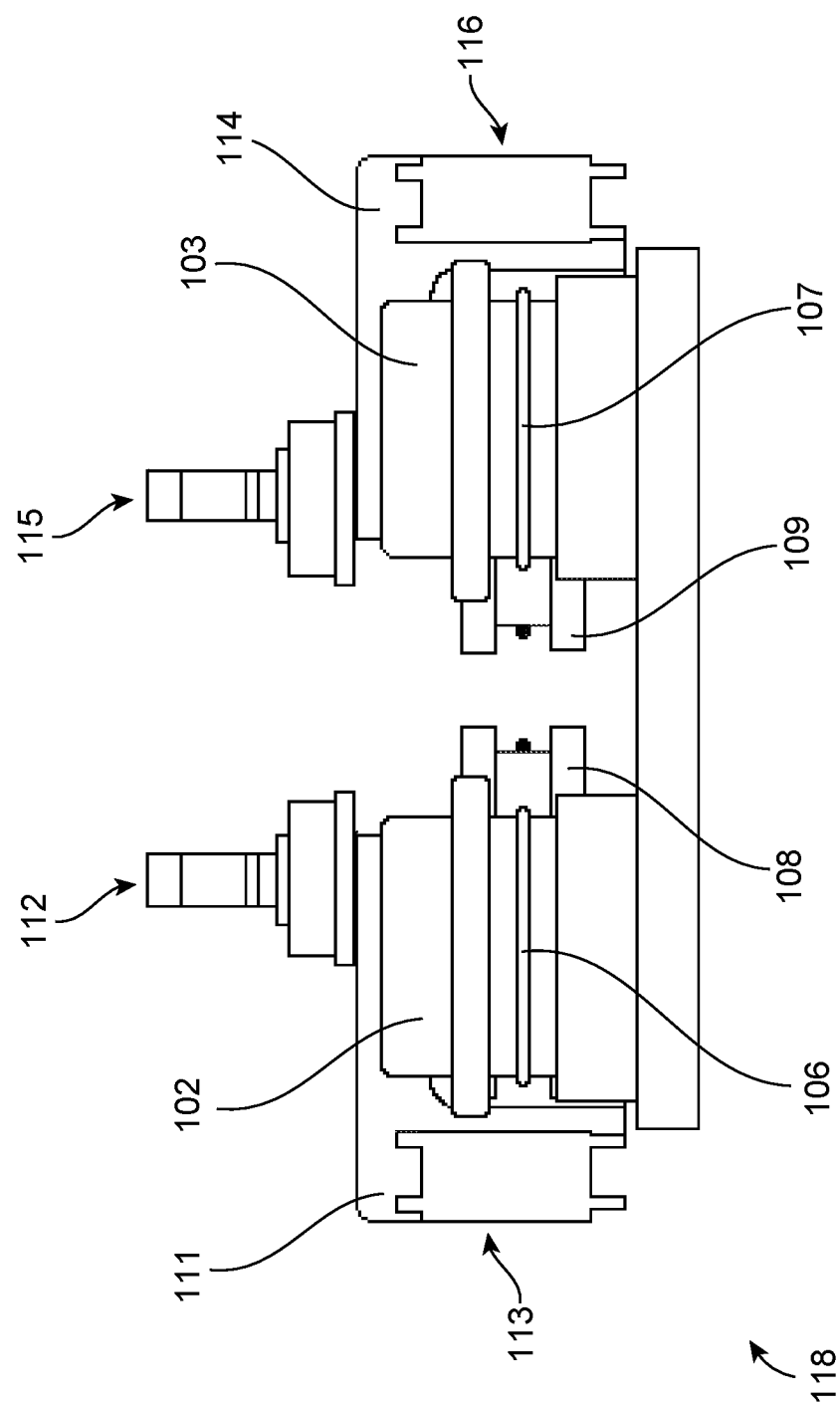
Figure 1E:
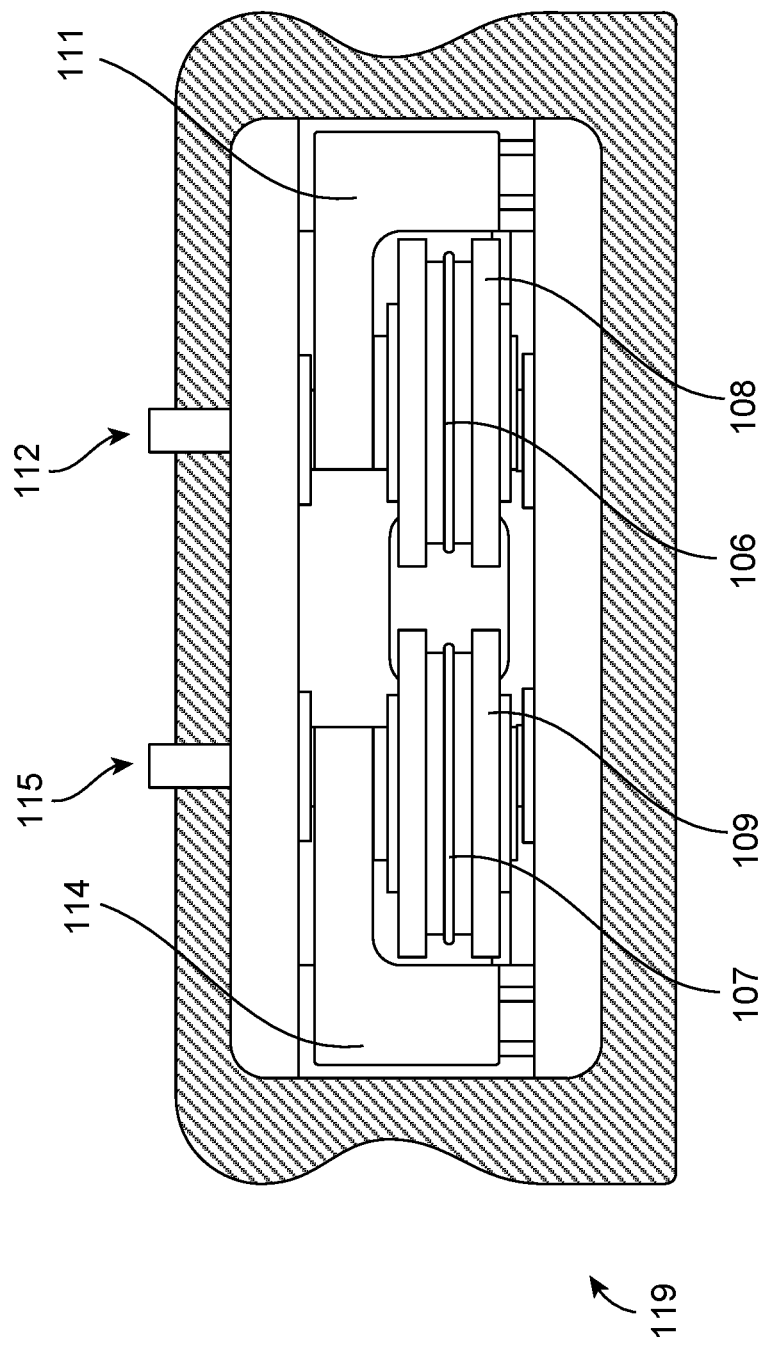
Figure 1G:
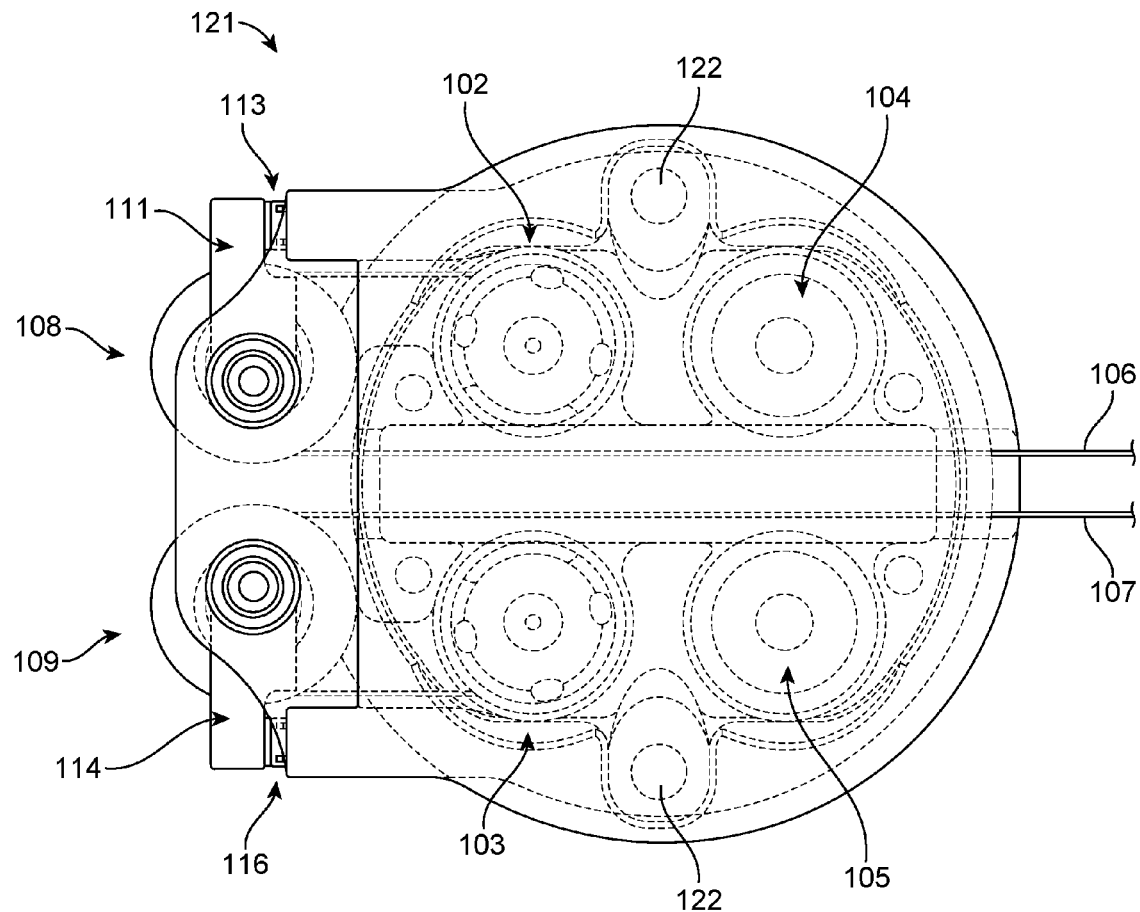

FIGS. 1C, 1D, 1E, 1F, 1G illustrate additional views of instrument 101 from FIGS. 1A, 1B, in accordance with an embodiment of the present invention. Side view 117 from FIG. 1C illustrates a side perspective of instrument 101 and the alignment of the tendons, spools, levers, and sensors within instrument 101, according to one embodiment. Front view 118 from FIG. 1D illustrates a frontal perspective of instrument 101 and the alignment of the spools and sensors within instrument 101, according to one embodiment. Partial cutaway view 119 from FIG. 1E illustrates a rear perspective of instrument 101 and the alignment of the spools and levers within instrument 101, according to one embodiment. Rear view 120 from FIG. 1F illustrates a rear perspective of instrument 101 and the alignment of the spools and levers, and their respective axes, without the exterior shell of instrument 101, according to one embodiment. Bottom cutaway view 121 from FIG. 1G illustrates a bottom-up perspective of instrument 101 and the alignment of the spools, levers, sensors within instrument 101, according to one embodiment. In addition, view 121 illustrates placement of magnets 122 that may be configured to couple instrument 101 to an interface or an instrument driving mechanism/instrument device manipulator.

Figure 2A:
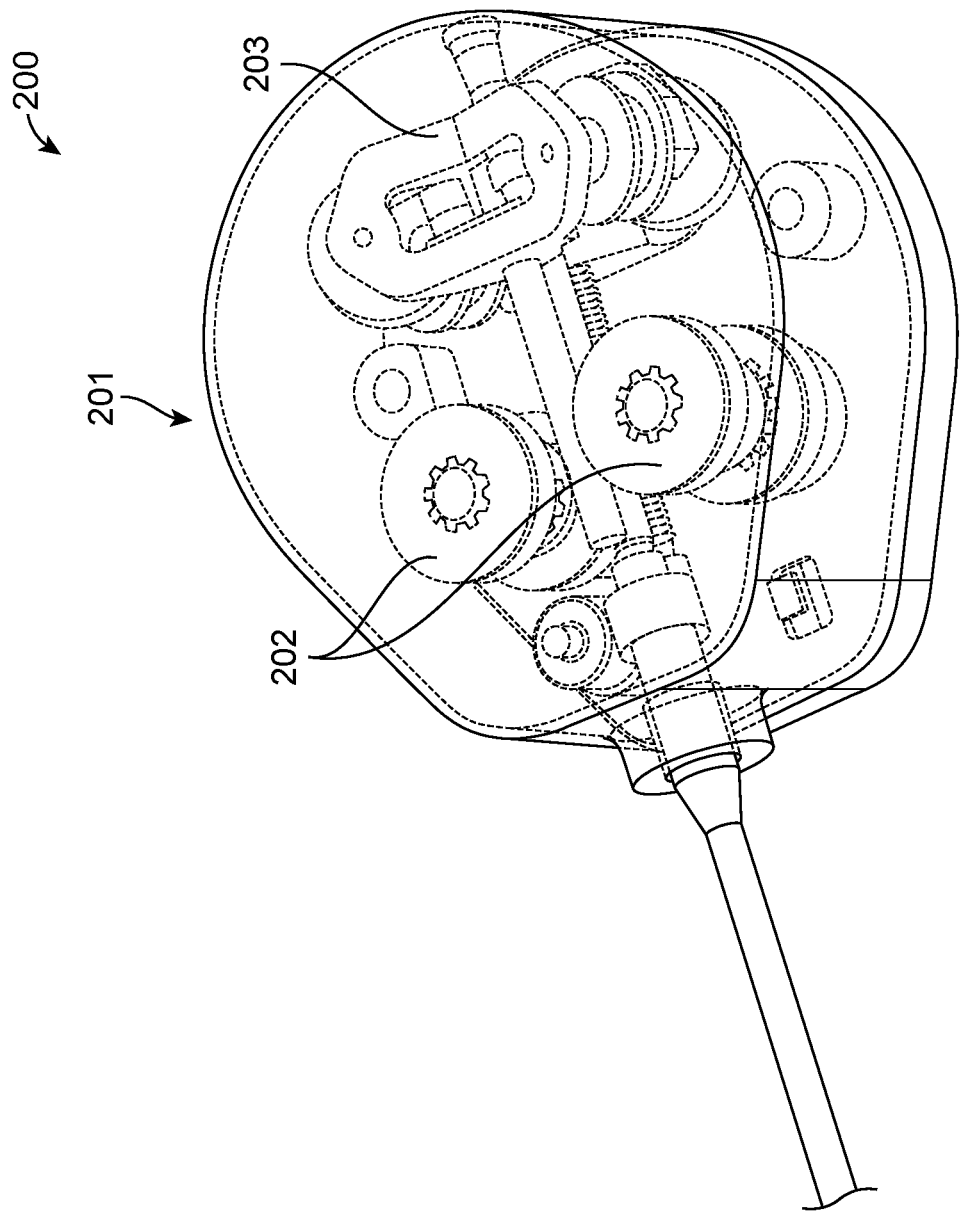
FIG. 2A illustrates an instrument that incorporates a tension sensing mechanism and is designed to actuate an elongated instrument, in accordance with an embodiment of the present invention.

FIG. 2A illustrates an instrument that incorporates a tension sensing mechanism and is designed to actuate an elongated instrument, in accordance with an embodiment of the present invention. In isometric view 200, instrument 201 receives rotational motion from an instrument device manipulator via coaxial drive shafts 202 to actuate tendons that are wound around redirect surfaces (i.e., idlers) that are located on an idler carriage 203, consistent with U.S. Provisional Patent Application No. 62/134,366, the entire contents of which are incorporated by reference.

Figure 2B:
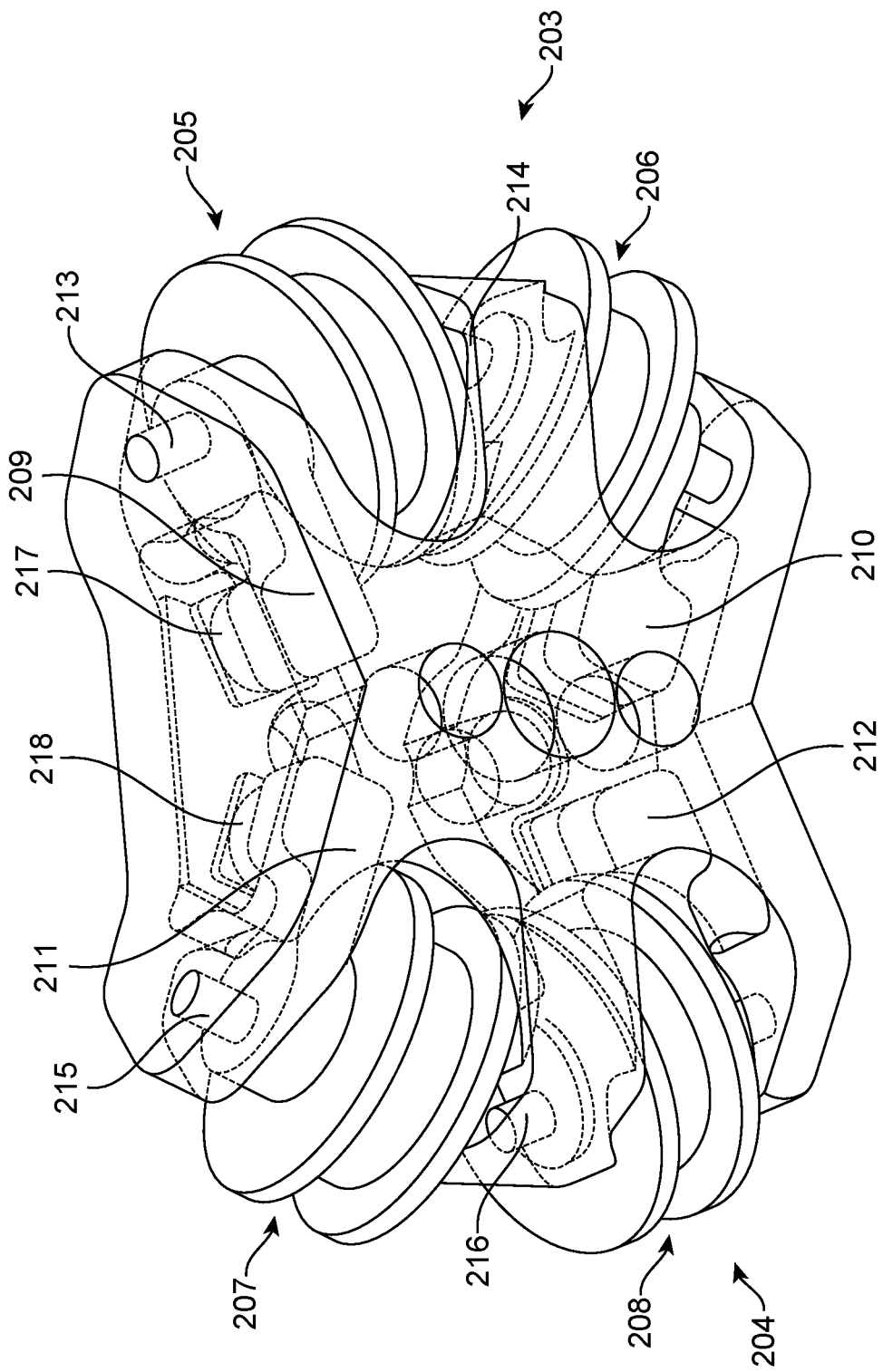
FIG. 2B illustrates the idler carriage of the instrument of FIG. 2A that incorporates a tension sensing mechanism, in accordance with an embodiment of the present invention.

FIG. 2B illustrates the idler carriage 203 from instrument 201 that incorporates a tension sensing mechanism, in accordance with an embodiment of the present invention. As shown in view 204, the idler carriage 203 generally comprises four rotatable bodies for redirecting tendons, i.e., pulleys 205, 206, 207, 208, where each of the pulleys is coupled to an individual lever element, such as levers 209, 210, 211, 212 respectively. Each lever 209, 210, 211, 212 includes a pivot axis, such as 213, 214, 215, 216 respectively, which is offset from the axes of pulleys 205, 206, 207, 208 respectively. In some embodiments, the axial offsets may be consistent and common to all the pulleys and levers in the idler carriage. In other embodiments, the axial offset between the levers and pulleys may vary within the idler carriage.

Consistent with previously disclosed embodiments, each lever in instrument 201 may be configured to provide reactive force to a corresponding sensor, such as sensor 217, which is configured to detect force exerted by lever 209 in response to tension on pulley 205. Similarly, sensor 218 is configured to detect force exerted by lever 211 in response to tension on pulley 207. Additional sensors are similarly situated relative to levers 210 and 212.

Figure 2C:
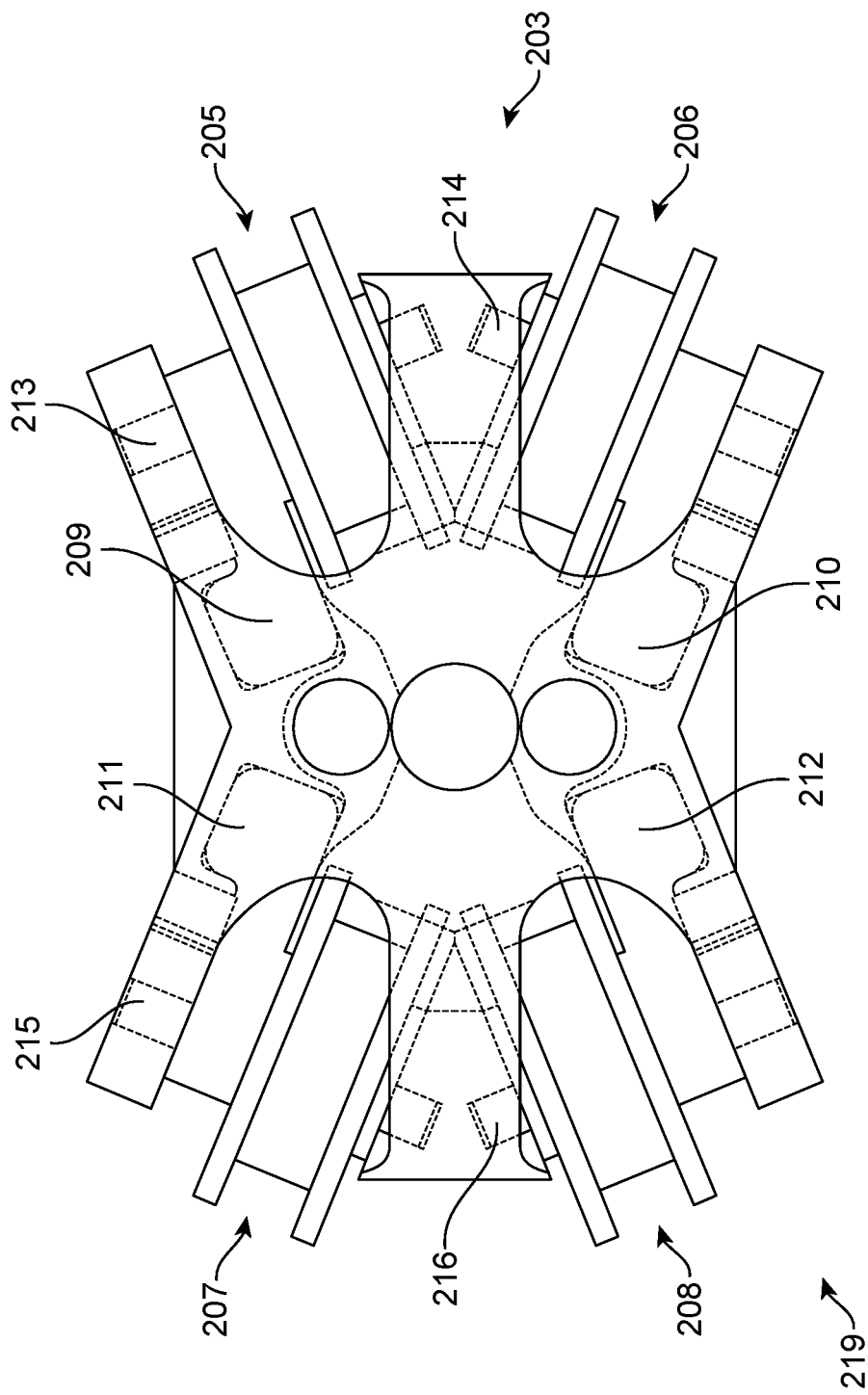
FIG. 2C illustrates the idler carriage of the instrument of FIG. 2A that incorporates a tension sensing mechanism, in accordance with an embodiment of the present invention.

FIG. 2C illustrates the idler carriage 203 from instrument 201 that incorporates a tension sensing mechanism, in accordance with an embodiment of the present invention. In contrast to view 204 from FIG. 2B, frontal view 219 from FIG. 2C provides a different perspective of the orientation of pulleys 205, 206, 207, 208, levers 209, 210, 211, 212 and pivot axes 213, 214, 215, 216 relative to each other.

Consistent with previously disclosed embodiments, each lever in instrument 201 may be configured to provide reactive force to a corresponding sensor, such as sensor 217, which is configured to detect force exerted by lever 209 in response to tension on pulley 205. Similarly, sensor 218 is configured to detect force exerted by lever 211 in response to tension on pulley 207.

Figure 2D:
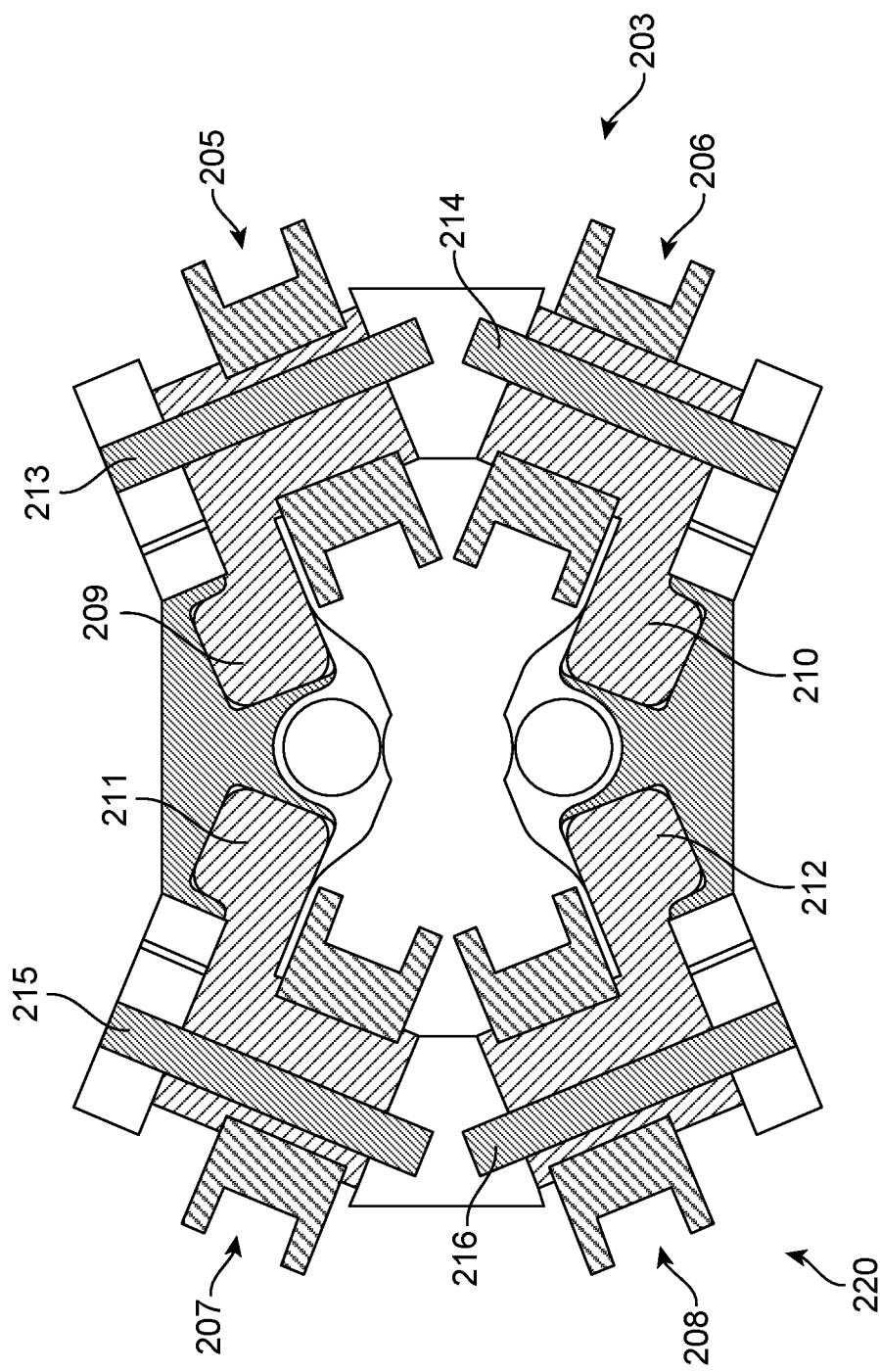
FIG. 2D illustrates a vertical cross-sectional view of the idler carriage of the instrument of FIG. 2A that incorporates a tension sensing mechanism, in accordance with an embodiment of the present invention.

FIG. 2D illustrates a vertical cross-sectional view of idler carriage 203 from instrument 201 that incorporates a tension sensing mechanism, in accordance with an embodiment of the present invention. As shown in cross-sectional view 220, pulleys 205, 206, 207, 208 may wrap around levers 209, 210, 211, 212 respectively to capture tension in the tendons that may be redirected around them. Additionally, the distal ends of the lever elements may be directed towards the center of the carriage where the sensors (not shown) are located.

Figure 2E:
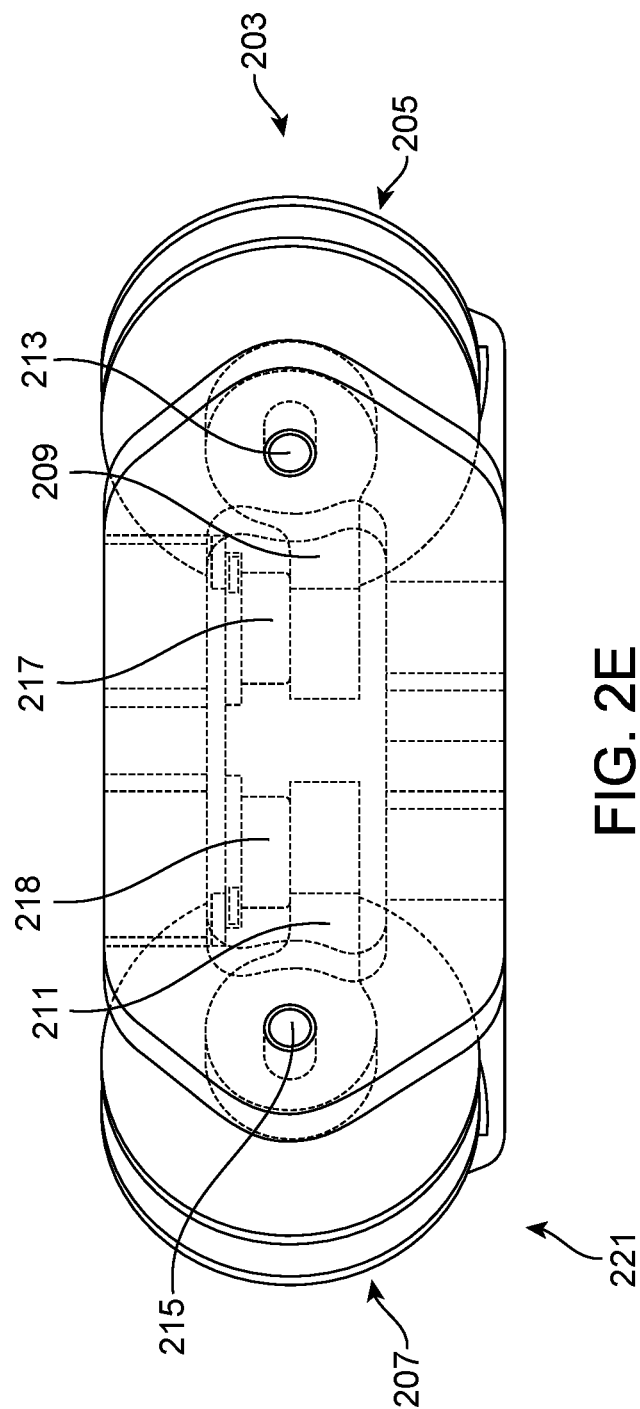
FIG. 2E illustrates an overhead view of the idler carriage of the instrument of FIG. 2A that incorporates a tension sensing mechanism, in accordance with an embodiment of the present invention.

FIG. 2E illustrates an overhead view of idler carriage 203 from instrument 201 that incorporates a tension sensing mechanism, in accordance with an embodiment of the present invention. As shown in top view 221, lever elements 209, 211 may be directed towards sensors 217, 218 respectively, located towards the center of the idler carriage 203, from opposite sides of idler carriage 203. Sensors 217, 218 may be configured to detect any force generated by levers 209, 211 respectively based on tension around pulleys 205, 207 respectively.

Figure 3:
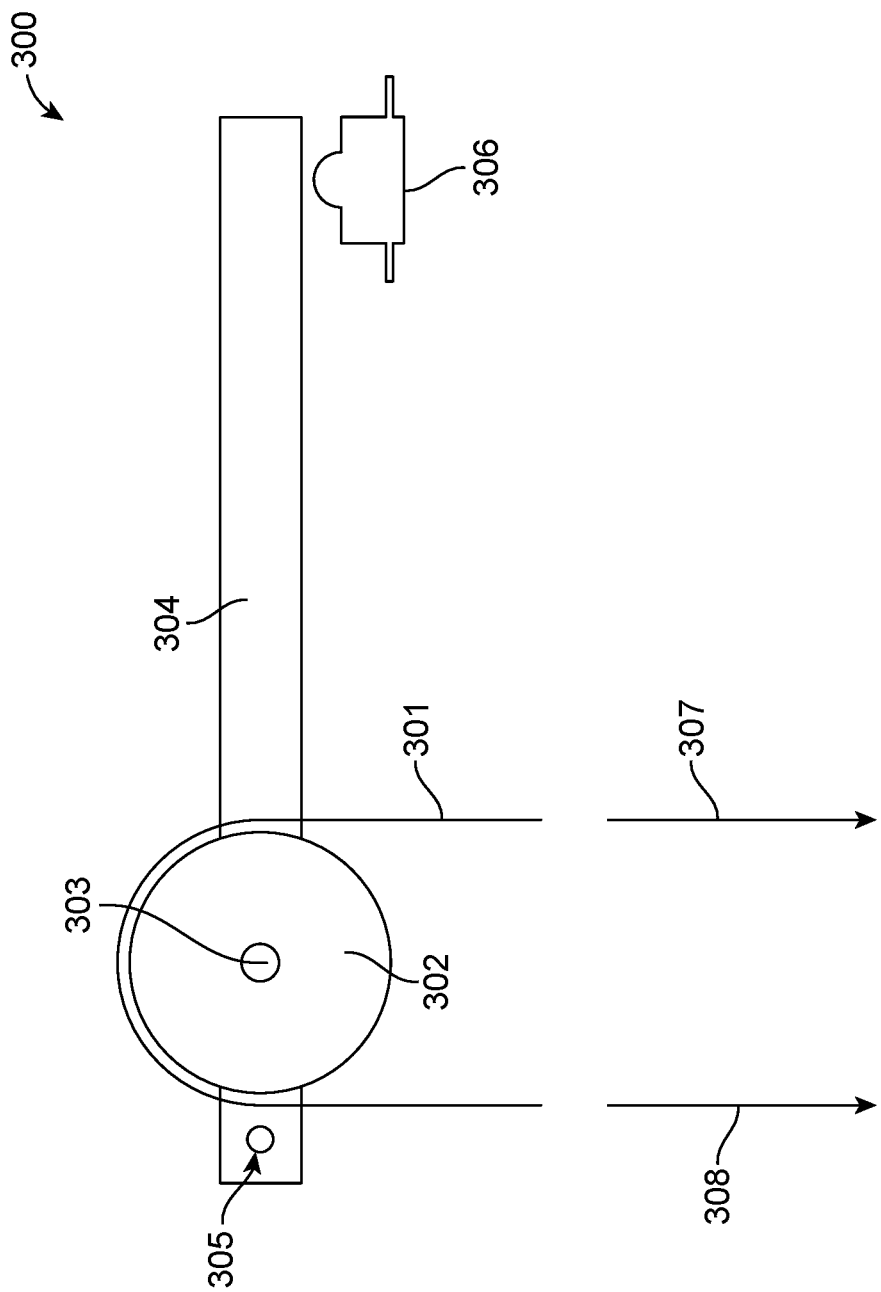
FIG. 3 illustrates a free body diagram representing the mechanical operation of a tension sensing apparatus, in accordance with an embodiment of the present invention.

FIG. 3 illustrates a free body diagram representing the mechanical operation of a tension sensing apparatus, in accordance with an embodiment of the present invention. As shown in view 300, the embodiment may generally comprise a tendon 301, a pulley 302 with a pulley axis 303, a lever element 304 with a pivot axis 305, and a sensor 306. Tension forces (represented as arrows 307 and 308) in tendon 301 exert equal and opposite forces along tendon 301 as it winds around pulley 302.

Given the known relationships between the location of the pulley 302, lever 304, and sensor 306, the tension in tendon 301 may be determined based on the measurement of force at sensor 306. Mathematically, the statics equilibrium may be expressed as:

$$\Sigma M_{Pivot} = 0 = (l_1+r)F_{Tension} + (l_1-r)F_{Tension} - l_2 F_{Sense} \quad \text{(Equation 1)}$$

where $\Sigma M_{Pivot}$ represents the sum of moments of lever 304 about the pivot axis 305, $F_{Tension}$ represents the tension force on the tendon 301, $l_1$ represents the distance from the pulley axis 303 pivot axis 305, $l_2$ represents the distance from pivot axis 305 to the point where the lever element 304 contacts the force sensor 306, r represents the radius of the pulley 302, and $F_{Sense}$ represents the force on the sensor 306.

With some algebraic manipulation, the expression may be reduced to determine the specific relationship between $F_{Tension}$ and $F_{Sense}$:

$$0 = l_1(2F_{Tension}) - l_2 F_{Sense} \quad \text{(Equation 2)}$$

$$l_2 F_{Sense} = l_1(2F_{Tension}) \quad \text{(Equation 3)}$$

$$F_{Tension} = \frac{l_2}{2l_1} F_{Sense} \quad \text{(Equation 4)}$$

where $l_1$ and $l_2$ are fixed constants based on the physical arrangement of the pulley 302, lever 304, and sensor 306. This mathematical relationship may also be applied with respect to the previously disclosed embodiments.

Figure 4:
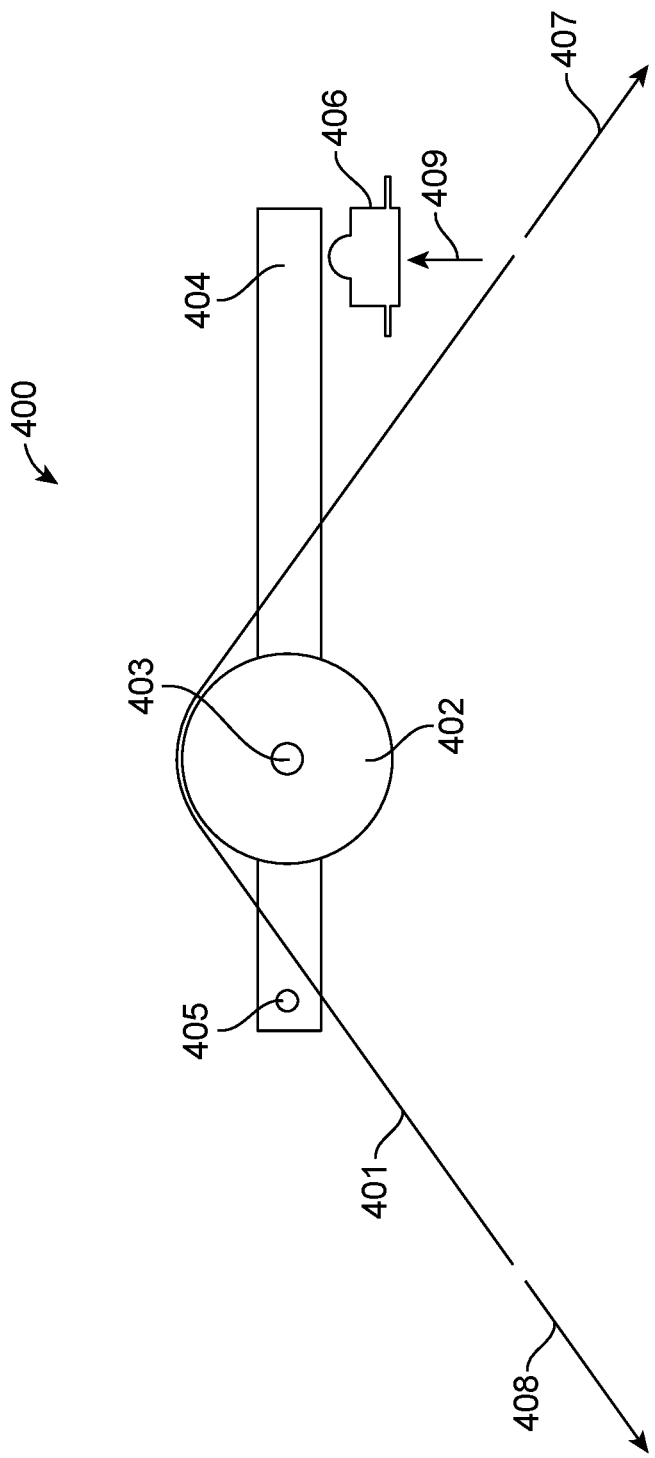
FIG. 4 illustrates a free body diagram representing the mechanical operation of a tension sensing apparatus, in accordance with an embodiment of the present invention.

The takeoff angle of the tendons is the angle at which the tendon comes off the pulley relative to the lever. The takeoff angle of the tendons in the example of FIG. 3 is 90 degrees. Where the takeoff angle of the tendons differs, the algebraic relationship described above may differ, but it still follows the same general principles. FIG. 4 illustrates a free body diagram representing the mechanical operation of a tension sensing apparatus, in accordance with an embodiment of the present invention. As shown in view 400, the embodiment may generally comprise a tendon 401, a pulley 402 with a pulley axis 403, a lever element 404 with a pivot axis 405, and a sensor 406. In view 400, tension forces $F_{Tension}$ (represented as arrows 407 and 408) in tendon 401 exert equal and opposite forces along tendon 401 as it winds around pulley 402. Unlike FIG. 3, however, the direction of the tendon 401 off of the pulley 402 is not orthogonal to the lever 404. As a result, the vector component of $F_{Tension}$ that runs parallel to $F_{Sense}$, represented as arrow 409 is calculated. Algebraic manipulation could then be used to derive the precise relationship between $F_{Tension}$ and $F_{Sense}$.

Figure 5:
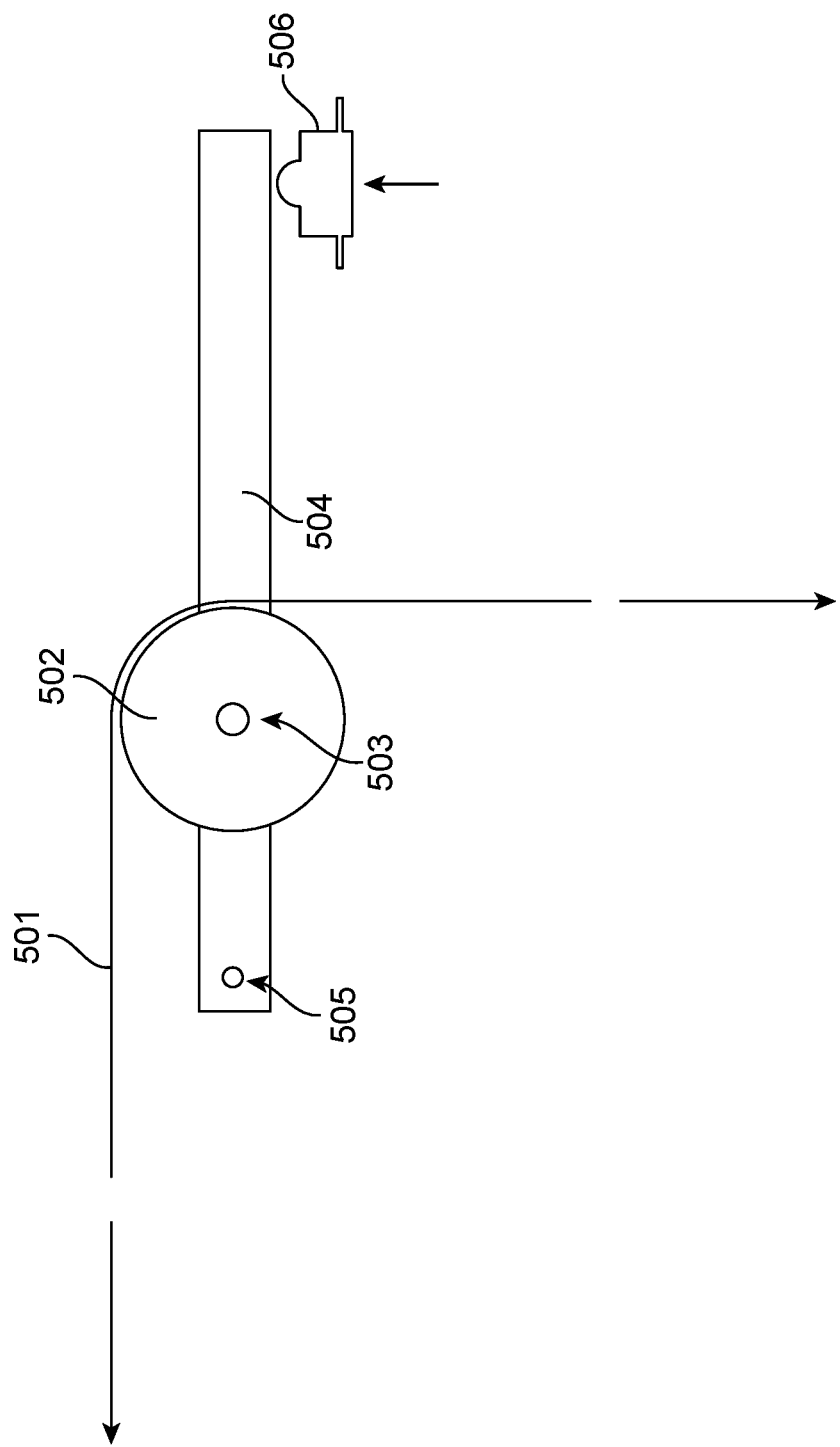
FIG. 5 illustrates a free body diagram representing the mechanical operation of a tension sensing apparatus, in accordance with an embodiment of the present invention.

The present invention also contemplates other embodiments where the takeoff angle differs for different tendons. FIG. 5 illustrates a free body diagram representing the mechanical operation of a tension sensing apparatus, in accordance with an embodiment of the present invention. As shown in FIG. 5, tension sensing may make use of an alternative arrangement of a tendon 501, a pulley 502 with a pulley axis 503, a lever element 504 with a pivot axis 505, and a sensor 506. For the embodiment of FIG. 5, where the tendon 501 "takes off" from the pulley 502 at different angles relative to the lever element 504, the vector components, if any, of $F_{Tension}$ that runs parallel to $F_{Sense}$ is evaluated to determine the relationship between those forces.

The aforementioned embodiments of the present invention may be designed to interface with an instrument drive mechanism and robotics platform such as those disclosed in the aforementioned patent applications that are incorporated by reference. For example, the embodiments in FIGS. 1A and 1B may be configured to be driven by an instrument drive mechanism or an instrument device manipulator that is attached to the distal end of a robotic arm through a sterile interface such as a drape. The driving elements may be shafts (male) or shaft receptacles (female) with spline interfaces to transfer rotational motion from the instrument drive mechanism to the instrument. As part of a larger robotics system, robotic control signals may be communicated from a remotely-located user interface, down the robotic arm, and to the instrument device manipulator to control the embodiment (instrument) of the present invention.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A medical device for performing minimally-invasive surgery comprising:
   an elongated instrument;
   a first elongated member coupled to the distal end of the elongated instrument, configured to actuate the distal end of the elongated instrument in response to tension in the first elongated member;
   a base located at the proximal end of the elongated instrument, the base comprising:
      a first redirect surface that redirects the first elongated member, the first redirect surface comprising a first rotatable body; and
      a first lever element that is coupled to the first redirect surface and configured to exert a reactive force on a first sensor in response to tension in the first elongated member, the first lever element coupled to the first redirect surface at a pivot point at a first location of the first lever element, the first lever element in contact with the first sensor at a second location of the first lever element, the pivot point of the first lever element offset from a rotation axis of the first rotatable body, wherein an axis of rotation of the first rotatable body is located between the pivot point and the first sensor.

2. The medical device of claim 1, wherein the first redirect surface is low friction.

3. The medical device of claim 1, wherein the base further comprises a second rotatable body, wherein the elongated member is threaded around the second rotatable body.

4. The medical device of claim 3, wherein rotational motion of the second rotatable body is configured to cause tension in the first elongated member.

5. The medical device of claim 3, wherein the second rotatable body comprises splines that receive rotational motion through a sterile interface from a robotic drive mechanism.

6. The medical device of claim 5, wherein the second rotatable body is a male connector.

7. The medical device of claim 5, wherein the second rotatable body is a female connector.

8. The medical device of claim 3, wherein a path of the first elongated member runs from the distal end of the elongated instrument past the second rotatable body, around the first rotatable body, and around the second rotatable body.

9. The medical device of claim 3, wherein a path of the first elongated member is perpendicular to an axis of rotation of the first rotatable body and an axis of rotation of the second rotatable body.

10. The medical device of claim 3, further comprising a second elongated member coupled to the distal end of the elongated instrument, configured to actuate the distal end of the elongated instrument in response to tension in the second elongated member.

11. The medical device of claim 10, the base further comprising:
   a second redirect surface that redirects the second elongated member, the second redirect surface comprising a third rotatable body; and
   a fourth rotatable body located between the second redirect surface and the distal end of the elongated instrument, wherein the second elongated member is threaded around the fourth rotatable body;
   wherein the second redirect surface is coupled to a second lever element that is configured to exert a reactive force on a second sensor in response to tension in the second elongated member.

12. The medical device of claim 11, wherein a path of the first elongated member is coplanar with a path of the second elongated member.

13. The medical device of claim 11, wherein a path of the first elongated member is not coplanar with a path of the second elongated member.

14. The medical device of claim 11, further comprising:
a third elongated member coupled to the distal end of the elongated instrument, configured to actuate the distal end of the elongated instrument in response to tension in the third elongated member; and
a fourth elongated member coupled to the distal end of the elongated instrument, configured to actuate the distal end of the elongated instrument in response to tension in the fourth elongated member.

15. The medical device of claim 14, the base further comprising:
a third redirect surface that redirects the third elongated member, the third redirect surface comprising a fifth rotatable body;
a sixth rotatable body located between the third redirect surface and the distal end of the elongated instrument, wherein the third elongated member is threaded around the sixth rotatable body;
wherein the third redirect surface is coupled to a third lever element that is configured to exert a reactive force on a third sensor in response to tension in the third elongated member;
a fourth redirect surface that redirects the fourth elongated member, the fourth redirect surface comprising a seventh rotatable body; and
an eighth rotatable body located between the fourth redirect surface and the distal end of the elongated instrument, wherein the fourth elongated member is threaded around the eighth rotatable body;
wherein the fourth redirect surface is coupled to a fourth lever element that is configured to exert a reactive force on a fourth sensor in response to tension in the fourth elongated member.

16. The medical device of claim 15, wherein the second and fourth rotatable bodies are coaxial and the sixth and eighth rotatable bodies are coaxial.

17. The medical device of claim 16, wherein the second and sixth rotatable bodies are coplanar and the fourth and eighth rotatable bodies are coplanar.

18. The medical device of claim 15, wherein the first and third rotatable bodies are not coplanar and have a first axial offset.

19. The medical device of claim 3, wherein the first and second rotatable bodies are coplanar.

20. The medical device of claim 3, wherein the second rotatable body is configured to receive rotational motion from a robotic drive mechanism.

21. The medical device of claim 3, wherein the second rotatable body is located between the first redirect surface and the distal end of the elongated instrument.

22. The medical device of claim 1, wherein the ratio of the tension in the first elongated member to the reactive force on the first sensor is fixed.

23. The medical device of claim 1, wherein the first lever element is configured to distribute the tension in the first elongated member between the pivot point and the first sensor.

24. The medical device of claim 1, wherein the elongated instrument is flexible.

25. The medical device of claim 24, wherein the elongated instrument is a catheter.

26. The medical device of claim 1, wherein the elongated instrument is rigid.

27. The medical device of claim 1, wherein the base is configured to interface with a robotic drive mechanism.

28. The medical device of claim 1, wherein the first elongated member is at least one of a wire, cable, and a tendon.

29. The medical device of claim 1, wherein the first sensor is at least one of a load cell, a piezoresistive device, a piezoelectric device, and a strain gauge.

* * * * *